United States Patent
Robert

(10) Patent No.: US 7,887,203 B2
(45) Date of Patent: Feb. 15, 2011

(54) MULTIPLE REFLECTION OPTICAL SYSTEM

(75) Inventor: Claude Robert, Orleans (FR)

(73) Assignee: Centre National de la Recherche Scientifiques - CNRS, Paris (FR)

( * ) Notice: Subject to any disclaimer, the term of this patent is extended or adjusted under 35 U.S.C. 154(b) by 401 days.

(21) Appl. No.: 11/997,638

(22) PCT Filed: Jul. 25, 2006

(86) PCT No.: PCT/FR2006/001814

§ 371 (c)(1),
(2), (4) Date: May 9, 2008

(87) PCT Pub. No.: WO2007/017570

PCT Pub. Date: Feb. 15, 2007

(65) Prior Publication Data

US 2008/0212217 A1  Sep. 4, 2008

(30) Foreign Application Priority Data

Aug. 5, 2005 (FR) .................................. 05 08396

(51) Int. Cl.
*G02B 5/10* (2006.01)
(52) U.S. Cl. ..................................... 359/858; 356/437
(58) Field of Classification Search ................ 359/850, 359/857, 858, 861; 356/432–444
See application file for complete search history.

(56) References Cited

U.S. PATENT DOCUMENTS 5,009,493 A * 4/1991 Koch et al. ................... 359/858

5,440,143 A 8/1995 Carangelo et al.

FOREIGN PATENT DOCUMENTS

EP  0 831 567 A1  3/1998

OTHER PUBLICATIONS

EPO International Search Report re PCT/FR2006/001814, completed Nov. 16, 2006, mailed Nov. 28, 2006.
D. R. Herriott, et al., "Folded Optical Delay Lines," Applied Optics, Aug. 1965, vol. 4, No. 8, pp. 883-890.
J. U. White, "Long Optical Paths of Large Aperture," Journal of the Optical Society of America, May 1942, vol. 32, No. 5, pp. 285-288.

* cited by examiner

*Primary Examiner*—Alessandro Amari
(74) *Attorney, Agent, or Firm*—Duane Morris LLP

(57) ABSTRACT

The invention relates to a multiple reflection optical system comprising a light beam input (E) and output (S) means, a first mirror (M1) having a curvature radius (R1) and arranged at a distance (d2) in front of a second mirror (M2) having a second curvature radius (R2) and arranged at a distance (d3) in front of a third mirror (M3) having a third curvature radius (R3), wherein the and second (M2) mirrors are arranged in such a way that formula (I) is satisfied and the first (M1) and third (M3) mirrors are arranged in such way that formula (II) is satisfied, the first (M1) second (M2) mirrors form a first optical cell having a first optical axis, the first (M1) and third (M3) mirrors form a second optical cell having a second optical axis, said first and second optical axes are different, the curvature radii (R1, R2, R3) and distances (d2, d3) are not simultaneously equal, said first and second optical cells are placed in such a way that the light beams are contained in the optical system between the input and output means.

9 Claims, 7 Drawing Sheets

MULTIPLE REFLECTION OPTICAL SYSTEM

The present invention relates to the optical field.

The present invention relates more particularly to the field of multiple reflection optical systems.

In the field of optical measurements by absorption, it is known to use a light source of intensity $I_0$ to illuminate a material to be analysed. The propagation in the absorbent material modifies the intensity according to an exponential law.

In the context of measuring the concentration of a gaseous species, this law is of the type $I=I_0\exp(-\sigma NL)$, $\sigma$ being the effective characteristic absorption cross section of the gas to be analysed, N being its concentration, and L being the length of the optical path.

It will therefore be understood that it is advantageous to increase the length of the optical path in order to improve the precision of the absorption measurements.

To do this, it is possible either to use long-distance sources and detectors or to use optical systems which are of a small size but allow a long optical path.

Multiple reflection optical systems are such systems.

In the field of multiple reflection optical systems, White cells have already been known in the prior art since the 1940s. As shown in FIG. 1, a White cell is composed of a first face comprising a mirror B and of a second face comprising two mirrors A and C. The mirrors are arranged in such a way that the radii of curvature of the three mirrors are equal to the distance between the mirrors, R1=R2=R3=D. By modifying the angle between the two juxtaposed mirrors A and C, it is possible to adjust the number of back-and-forth movements of the light beam and therefore to adjust the optical path.

However, such a White device has the disadvantage of not using the entire useful surface of the mirrors, since all the rays pass via the centres of the mirrors A and C and on two lines of the mirror B. This is a consequence of the constricting symmetry condition R1=R2=R3=D.

It would therefore be advantageous, in order to increase the number of back-and-forth movements of the light, to use the entire surface of the mirrors of the optical cell.

For a different purpose, there has already been proposed, in the publication "Optical True time delay for phased array antennas: demonstration of a quadratic White Cell" (Betty Lise Anderson and Craig D. Little), a system comprising a combination of two White cells and a means for making the rays pass from one cell to the other, for example of the MEM or beam splitter type. The second White cell is composed of two mirrors which are of different radii of curvature but satisfy the White condition, i.e. that the radii of curvature of the two mirrors are equal to their respective distances from the beam splitting device. The disadvantages of the White cell are therefore also found in the device described in the publication mentioned above.

The prior art has also known, since the 1960s, Herriott cells composed of two mirrors opposite one another, one of the mirrors being pierced by a hole for allowing the light beam to enter the cell. As shown in FIG. 2, the beam enters the cell through the hole pierced in M1 and undergoes multiple reflections on the two mirrors. The traces on the mirrors form ellipses.

For some values of the distance between the mirrors, the beam exits again through the hole pierced in M1. These remarkable configurations are referred to as the operating point. Thus the operating conditions of a Herriott cell generalised to mirrors having different radii of curvature are obtained when the distance between the mirrors is such that two mutually prime whole numbers K and N exist such that:

$$\cos\left(\frac{K\pi}{N}\right) = \sqrt{\left(1 - \frac{d}{R_1}\right)\left(1 - \frac{d}{R_2}\right)}$$

d being the distance between the mirrors,
R1 being the radius of curvature of the mirror M1,
R2 being the radius of curvature of the mirror M2.

It will be noted that this device is very stable since the operating point is not very dependent on the attitude of M1 and is not dependent at all on the attitude of M2, and the mirrors M1 and M2 can then move slightly or even vibrate without the exit of the beam being affected. Furthermore, it is easy to implement since it comprises only two mirrors.

Once again, however, the whole surface of the mirrors is not used, and this configuration does not allow a large number of back-and-forth movements between the mirrors.

More generally, it is known that in a multiple reflection device comprising two mirrors opposite one another with radii of curvature R1 and R2 and located at a distance d from one another, the stability condition which makes it possible for the light beams to be kept in the cell can be written:

$$0 < \left(1 - \frac{d}{R_1}\right)\left(1 - \frac{d}{R_2}\right) < 1$$

This well-known condition is described for example in the publication "Laser Beams and Resonators" by Hogelnik and Li, in Applied Optics, Volume 5, Number 10, October 1966.

The aim of the present invention is therefore to propose a stable multiple reflection optical system which makes it possible to increase the number of back-and-forth movements between the mirrors of the cell in order to increase the length of the optical path of the light beam, while retaining satisfactory optomechanical stability.

To this end, the present invention relates to a multiple reflection optical system comprising a light beam input means E and an output means S, a first mirror M1 having a radius of curvature R1, said first mirror being arranged opposite and at a distance d2 from a second mirror M2 having a second radius of curvature R2 and opposite and at a distance d3 from a third mirror M3 having a third radius of curvature R3, the first mirror M1 and the second mirror M2 being arranged in such a way that $$0 < \left(1 - \frac{d_2}{R_1}\right)\left(1 - \frac{d_2}{R_2}\right) < 1$$

and the first mirror M1 and the third mirror M3 being arranged in such a way that $$0 < \left(1 - \frac{d_3}{R_1}\right)\left(1 - \frac{d_3}{R_3}\right) < 1,$$

the first mirror M1 and the second mirror M2 forming a first optical cell having a first optical axis, the first mirror M1 and the third mirror M3 forming a second optical cell having a second optical axis, said first and second optical axes being separate, the radii of curvature R1, R2, R3 and the distances d2 and d3 not being simultaneously equal, said first and second optical cells being arranged in such a way that the light beam is contained in the optical system between the input means and the output means.

It will be understood that if the mirrors M2 and/or M3 are flat and the mirror M1 is spherical, the optical axes are defined by the straight line passing through the centre of curvature of M1 and normal to the plane of M2 and/or M3.

In the case of a cell formed by spherical mirrors, this optical axis is the straight line passing through the centres of curvature of the two mirrors of the cell.

According to one particular embodiment, the first and second mirrors M2 and M3 are located at an equal distance d from the first mirror M1, and their radii of curvature R2 and R3 are substantially equal to a common radius R. The two cells defined on the one hand by the first mirror M1 and by the second mirror M2 and on the other hand by the first mirror M1 and by the third mirror M3 are then arranged in such a way as to verify the Herriott operating conditions which for each cell can be written: two mutually prime whole numbers K and N exist such that:

$$\cos\left(\frac{K\pi}{N}\right) = \sqrt{\left(1 - \frac{d}{R_1}\right)\left(1 - \frac{d}{R}\right)}.$$

This configuration gives the system great optomechanical stability as in the case of a simple Herriott cell.

The second and third mirrors according to the invention in fact define two Herriott cells. This is because the rotation of one of the two mirrors causes the displacement of its centre of curvature, which multiplies the reflections compared to a known Herriott cell. It will be demonstrated below that the inclination of one mirror relative to the other causes a displacement of the exit point for the beam which, instead of leaving the cell as in a Herriott cell, recirculates in the cell and thereby increases the number of back-and-forth movements of the beam.

Compared to a White cell, the system according to the invention also has the advantage of not requiring that the radii of curvature of the mirrors are equal to the distance between the two ends of the cell. The operating point is therefore achieved even outside a confocal system.

Preferably, in order to be able to vary the number of reflections within the cell, said inclination is variable and the optical system also comprises a means for rotating at least one of said second and third mirrors relative to the other.

According to a first embodiment which is particularly simple, the system is composed of a first mirror in the form of a spherical mirror, and the second and third mirrors are flat mirrors which are inclined relative to one another.

According to another embodiment, the system is composed of a first mirror in the form of a spherical mirror, and the second and third mirrors correspond respectively to the lower part and to the upper part of one and the same spherical mirror that has been cut, one of the lower or upper parts being inclined relative to the other.

Preferably, the second mirror M2 and the third mirror M3 each have a straight edge and are joined by said edges and without touching one another, said edges being substantially parallel to the line passing through the intersection of the two optical axes with the second mirror M2 and the third mirror M3. Advantageously, the light beam input means E is positioned in such a way as to generate a row of substantially focused reflection points along the edge of at least one of said second M2 and third mirrors M3.

In this way, advantage can be taken of the optomechanical stability of the system, in particular for the manipulations carried out. Since the focusing points are linked to the entry point, it can be ensured that they are kept on the edge of one of the mirrors.

The invention will be better understood with the aid of the description, given below purely by way of example, of one embodiment of the invention, with reference to the appended figures.

Figure 1:
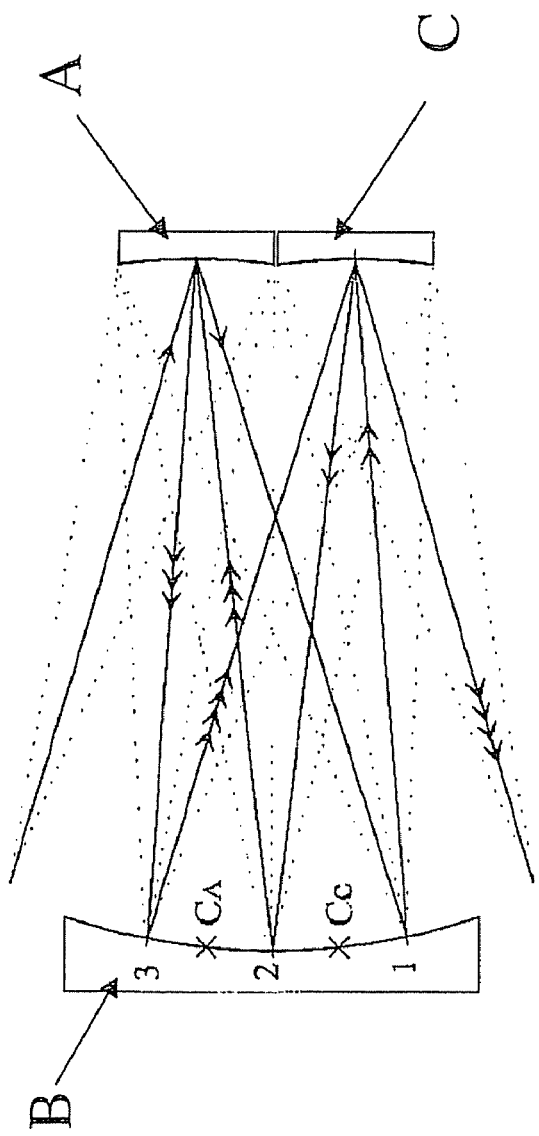
FIG. 1 shows a White cell known from the prior art.
Figure 2:
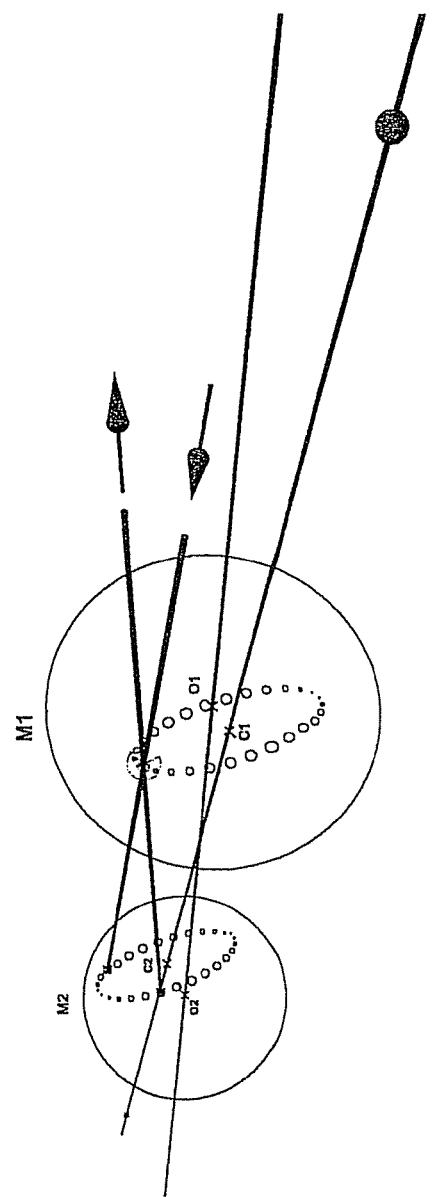
FIG. 2 shows a Herriott cell known from the prior art.

Firstly the mode of operation of a known cell of the Herriott type as shown in FIG. 2 will be recalled.

As shown in FIG. 2, the beam enters the cell through the hole pierced in M1. The beam undergoes multiple reflections on the two mirrors. The traces on the mirrors form ellipses.

For some values of the distance between the mirrors, the beam exits again through the hole pierced in M1. These remarkable configurations are referred to as the operating points. In general, when the radii of curvature are different, the operating points are obtained when the distance between the mirrors is such that two mutually prime whole numbers K and N exist (mutually prime=no common divisor other than 1) such that:

$$\cos(K\pi/N) = \sqrt{g_1 g_2} \text{ and } g_1 = 1 - \frac{d}{R_1} \text{ and } g_2 = 1 - \frac{d}{R_2}$$

N is the number of back-and-forth movements carried out by the beam in the cell. It is also the number of reflections on one of the mirrors.

K is the number of turns of the beam about the optical axis.

d being the distance between the mirrors,

R1 being the radius of curvature of the mirror M1,

R2 being the radius of curvature of the mirror M2.

In the case where the mirrors located opposite one another have identical radii of curvature, then $g1=g2=1-d/R$ $g1/g2=1$ The operating points are obtained when:

$d=R(1-\cos\theta)$ where $\theta=K\pi/N\ \theta\in[0,\pi]$

This has different consequences described below:

The traces of the reflections on the two mirrors form homothetic ellipses in the ratio $$\sqrt{\frac{g_1}{g_2}}.$$

These ellipses are centred on the optical axis of the system which is the straight line passing through the centres of curvature of the two mirrors.

The diameter of these reflection spots follows a sinusoidal evolution when running through the ellipse. The diameters of these spots on the two mirrors are in the same ratio $$\sqrt{\frac{g_1}{g_2}}.$$

This evolution shows that, on each mirror, two reflection spots which are symmetrical with respect to the optical axis have the same diameter.

The ruled surface brought about by the beams is a hyperboloid.

The whole cell is equivalent to a divergent spherical mirror, the surface of which coincides with that of M1 (the beam exits again from the cell as if the entering beam were reflected on the surface of M1).

It will also be noted that when the entry point is a focusing point, the exit point is also a focusing point.

The consequence of this is that the emerging beam is independent of the orientation of M2: the ellipses deform but the exit beam remains immobile.

As in a confocal Fabry-Perot, the aberrations of the system are of the fourth order. The optical path difference between a beam passing through the system on the optical axis and a beam outside the axis is given by:

$$L - 2Nd \approx \frac{Nr^4}{dR^2}$$

where L is the total optical path and r is the main axis of the ellipsis of the traces of reflections (case where R1=R2).

In the case where the reflections are located on circles, θ and K have simple geometric interpretations:
- the reflection points are uniformly spaced apart around the circle,
- two successive reflections are separated by K intervals (K−1 reflection spots),
- the angle between two successive reflections is 2θ,
- K is the number of turns of the reflections about the optical axis.

When the entering beam is a parallel beam, the diameter of the spots varies from a minimum value which may be zero to a maximum value which is close to $$1 \Big/ \cos\left(\frac{\theta}{2}\right)$$

times the diameter of the entering beam.

Furthermore, when the distance between the mirrors (or the radius of curvature) changes, all of the traces of reflections slide on the ellipse proportionally to their reflection index. The exit point is therefore the point which moves the most. It is displaced tangentially to the ellipse of the reflections.

In the text which follows, we will consider only the case where the mirrors have an identical radius of curvature in order to simplify the formalism and reasoning by holding that this cell operates in an identical manner with different radii of curvature.

Still in order to simplify the explanation, we will consider a Herriott cell in which the reflections are located on a circle with the cases where K=1 as the operating points.

Given the properties of the Herriott cell, each reflection is contiguous with the previous and the subsequent reflection. The N/2 first reflections are located on the same half of the mirror. In FIG. 2, M1 is the mirror via which the beams enter and leave and M2 is the other mirror.

Figure 3:
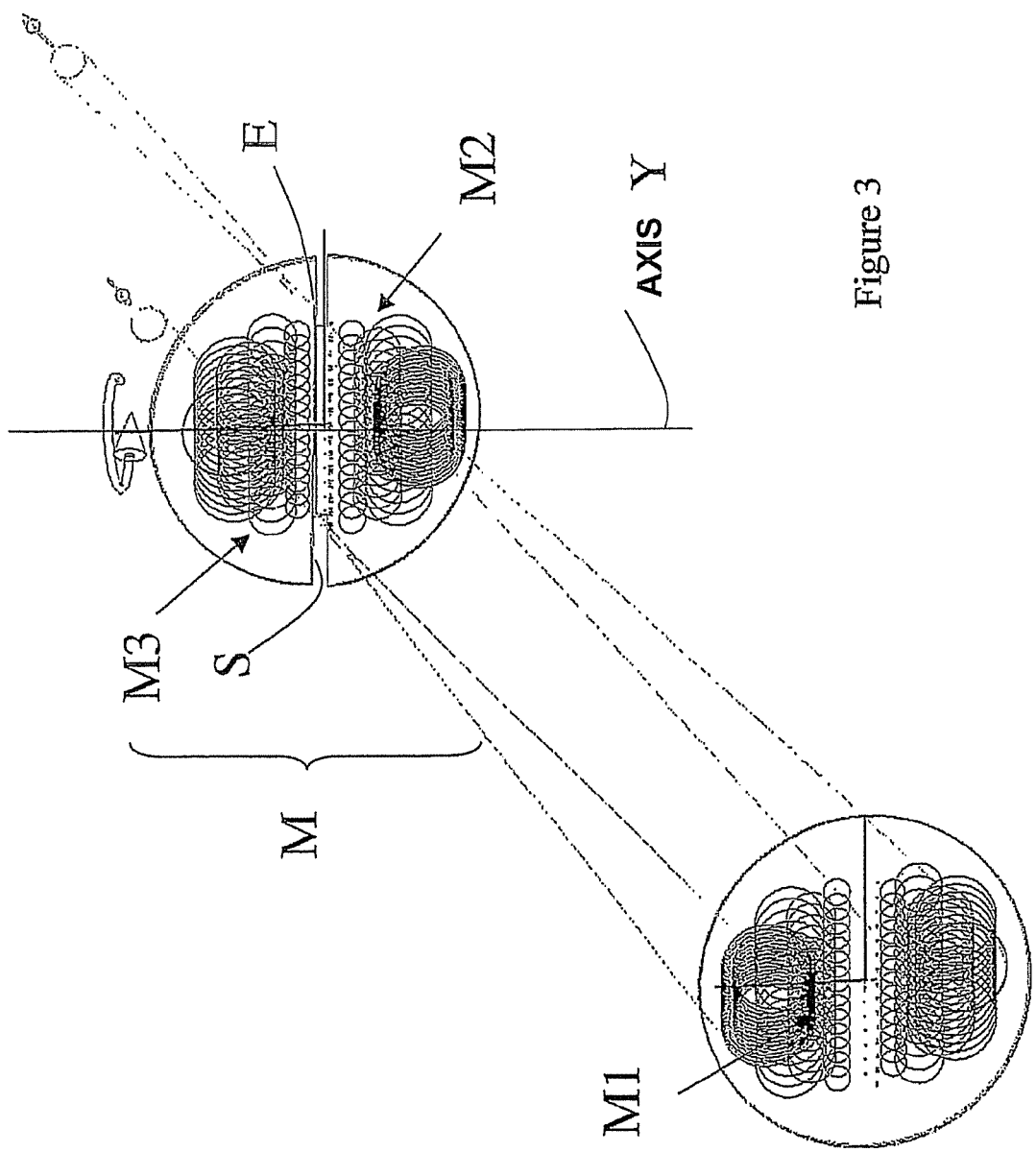
FIG. 3 shows an example of a multiple reflection cell according to the invention.

By cutting the mirror just above the injection point, and by pivoting one of the halves which we will call M3 as shown in FIG. 3, a second Herriott cell is created. This is because the rotation of this mirror causes the displacement of its centre of curvature. A new optical axis is created which passes through the centre of curvature of M3 and M1.

Being assumed that X is the axis which separates the two mirrors, Y is the perpendicular axis and Z is the axis which passes through the centre of the mirrors M2 and M1, if M3 is turned about the axis Y, then its centre of curvature is displaced in a plane perpendicular to the axis Y (plane XOZ) and consequently the intersection of the new optical axis with M3 is displaced on the axis X.

As shown in FIG. 4, the consequences of this configuration on the reflections will now be studied. The first half of the reflections remains unchanged: they are still located on a half-ellipsis which is symmetrical with respect to the intersection (C2) of the optical axis of the first cell with M2.

When the beam arrives on M3 for the first time, it enters a new cell. This first reflection serves as an entry point for the new cell.

The second half of the reflections then uses the new cell and thus generates a second half-ellipsis which is symmetrical with respect to the intersection (C3) of the optical axis of the second cell with M3.

Figure 4B:
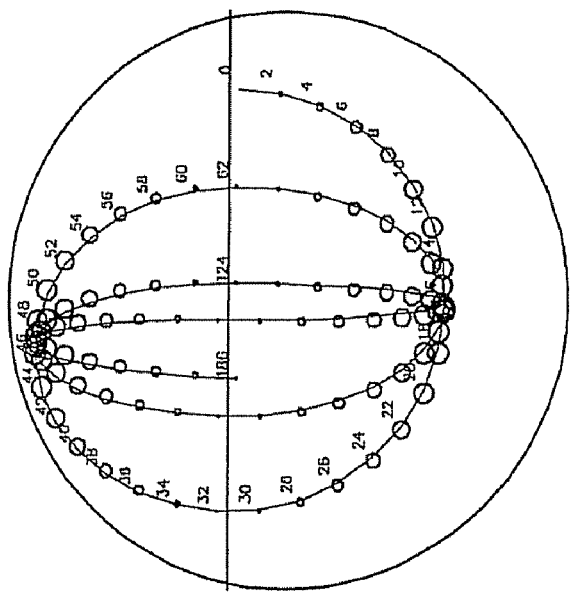
FIGS. 4A and 4B show an example of the path of the light reflections in a cell according to the invention.
Figure 4A:
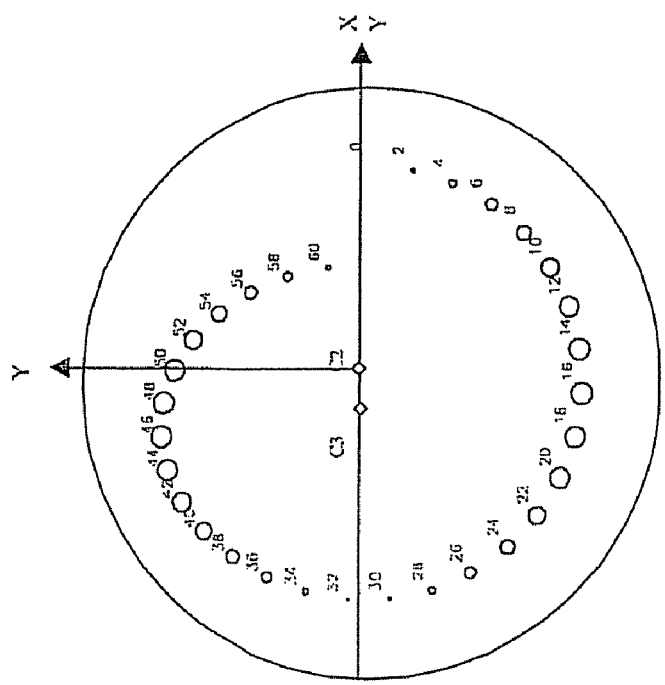

This is illustrated in FIGS. 4A and 4B for a cut Herriott mirror where K=1 and N=31.

The mirror M is cut into two on the X axis.

The upper half is inclined (rotation about the Y axis).

The new optical axis passes through C3 and the following reflections are on an ellipsis which is symmetrical with respect to this new axis.

In the context of modelling a Herriott cell in the Gauss approximation when the reflections are located on a circle, the position of the $i^{th}$ reflection on the Y axis is given by:

$$y_i = -x_0 \sin(i\theta).$$

In our case, in projection on the plane YoZ, there is no modification of the parameters for the new cell. Since the equations projected onto the planes XoZ and YoZ which describe the evolution of the ray are independent, the position on Y of the reflection points remains unchanged.

It therefore follows from this that the following dimension Y of the new half-ellipsis is independent of the rotation of M3 and is therefore the same as for a zero rotation.

Similarly, it can be deduced that if the entry point is a focusing point, the exit point in a conventional Herriott cell is also a focusing point. For the new cell, since there is always focusing in projection on the Y axis, there is necessarily also focusing for the X axis: if the entry point is a conjugate of the exit point on one axis, it must also be on the other too.

Finally, the result of the inclination of the half-mirror M1' leads to a displacement of the exit point only on the X axis by twice the distance separating the intersections of the optical axes of the two Herriott cells with M2 and M3.

After having carried out the second half of its reflections, the focused beam again reaches the first mirror of the first cell, the beam then continues to pass through the cell. The ellipses become closer and closer until one of them passes between the two optical centres. The direction of rotation of the ellipses is then reversed (FIG. 4A).

At this point, it is possible either to allow the reflections to continue until one of the refocusing points leaves the first half-circle of reflections, or to modify the injection angle or the inclination of the mirror M1.

It is then easy to inject the beam into the cell through a hole located on one of the sides of the lower half-mirror and to recover the beam when it exits through a diametrically opposed hole. Once in this configuration, the adjustment of the inclination of the half-mirror controls the multiplying coefficient of the number of reflections of the initial Herriott cell obtained for a zero inclination. It is remarkable to note that, once the position of the exit hole is fixed, the exiting beam always retains the same direction regardless of the selected multiplying coefficient.

By considering that K is the number of turns carried out by the reflections about the optical centre, it is easy to see that during the N reflections the beam passes K times from the lower part of M to its upper part. The ellipses are therefore modified K times during the first path. As a first approximation, the exit point is therefore shifted by 2K times the distance between C2 and C3. Rigorous modelling that can easily be carried out by the person skilled in the art shows that this is not perfectly accurate but increases in accuracy as N increases. However, it is of little importance to know the exact expression; the important thing is that, here too, the half-mirror adjustment causes a displacement of the exit point which allows its recirculation in the cell.

Figure 5:
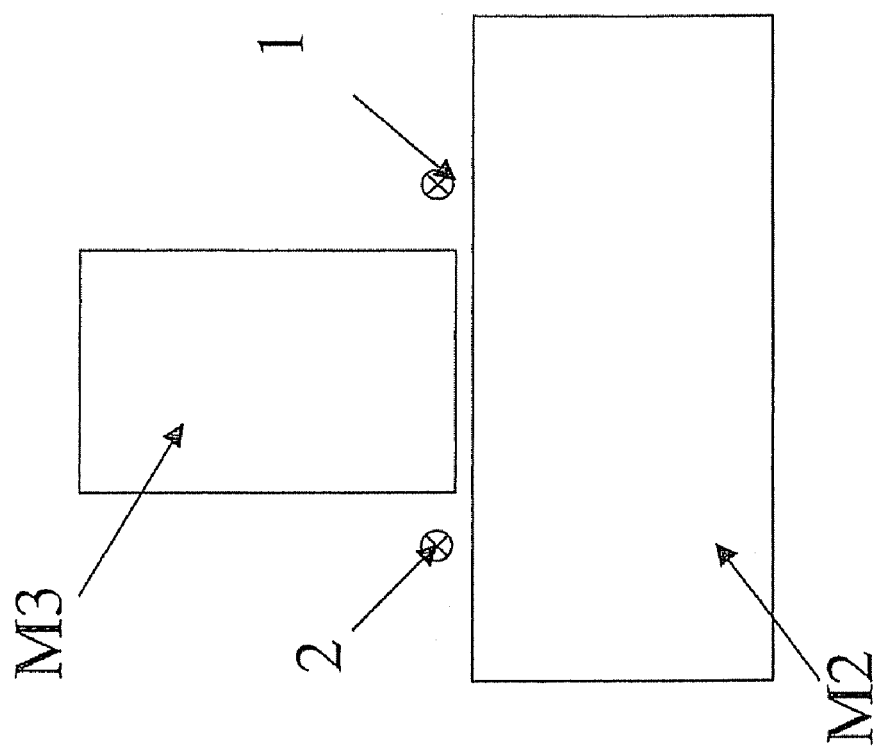
FIGS. 5 and 6 show an example of embodiment of the mirrors which can be inclined in a cell according to the invention.
Figure 6:
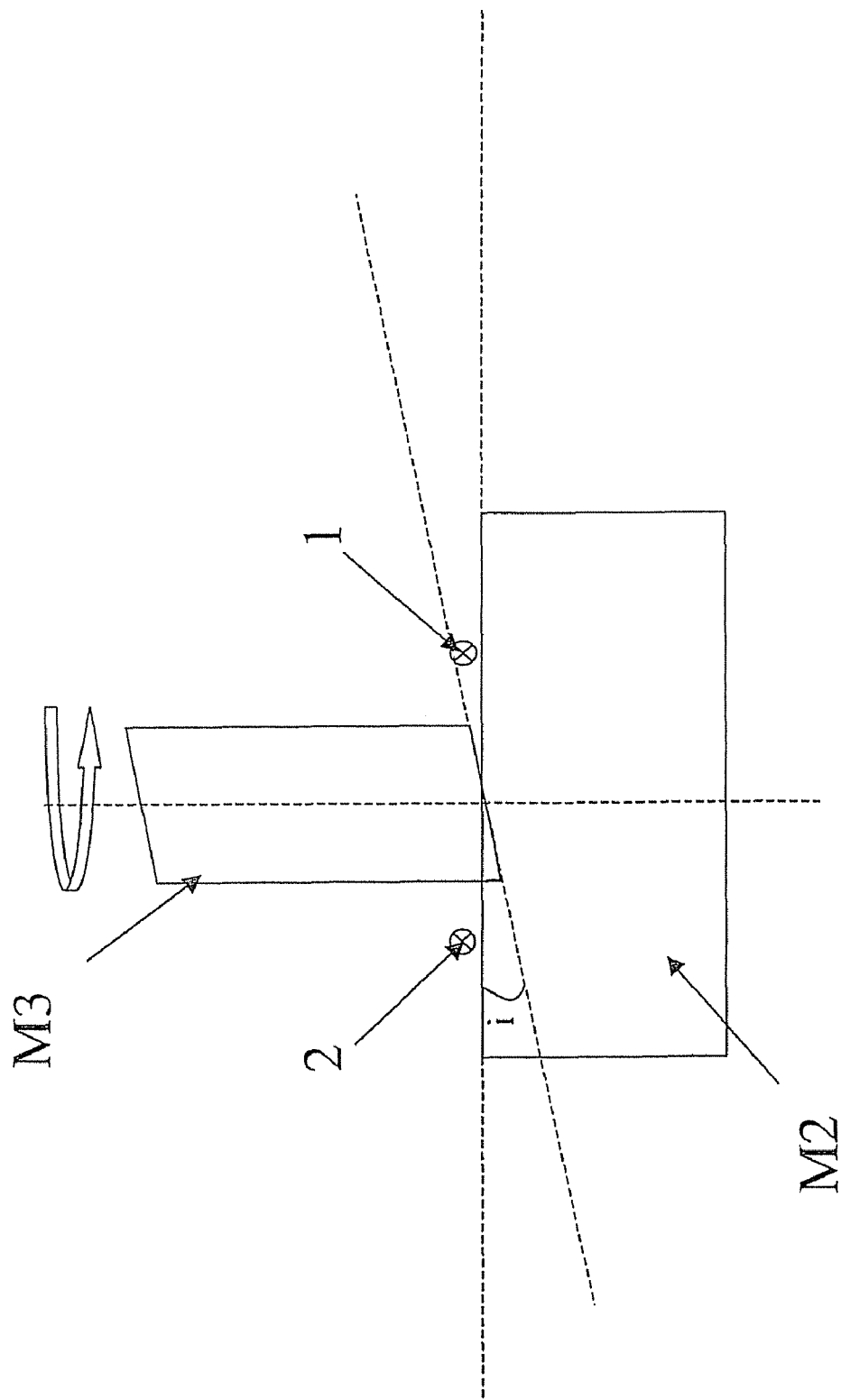
Figure 7:
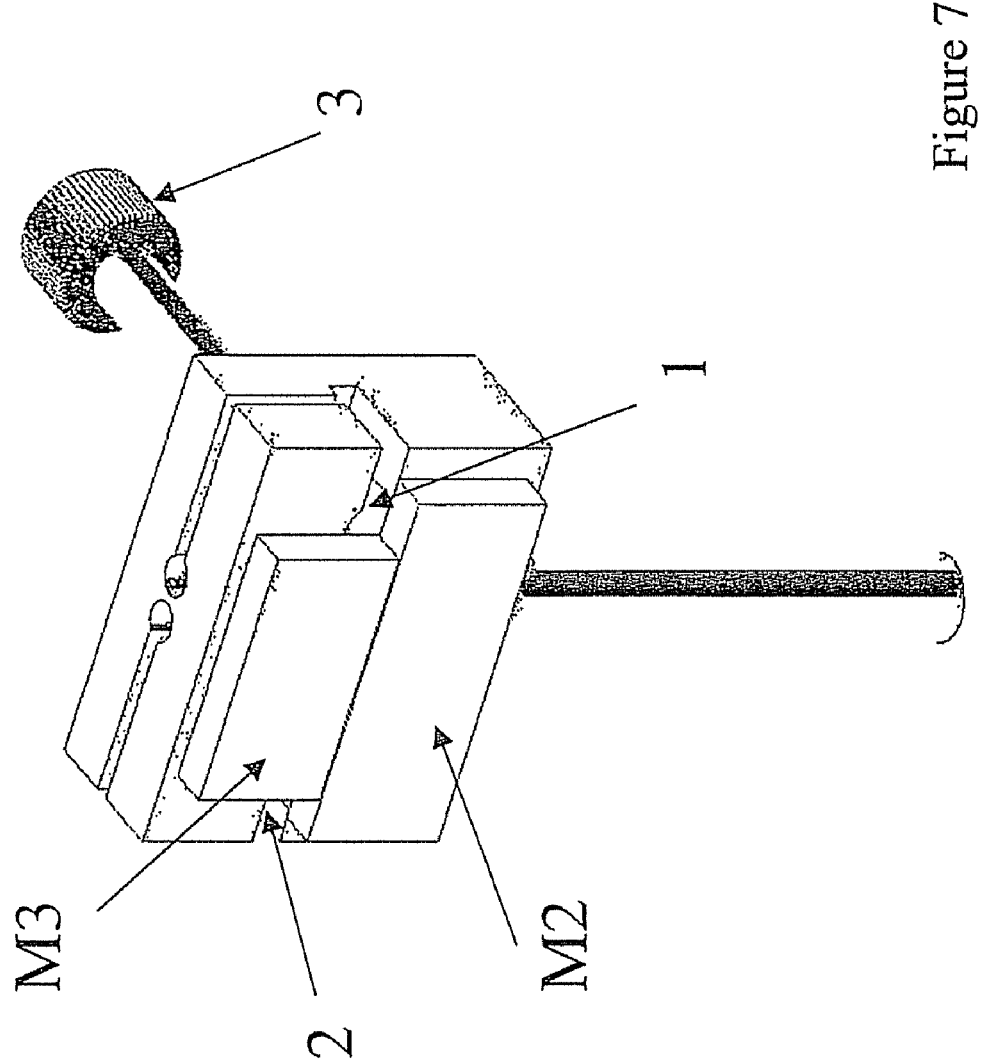
FIG. 7 shows an example of a device for inclining the mirrors according to the invention.

As illustrated in FIGS. 5 and 6, an embodiment which uses two flat mirrors and one spherical mirror will now be described.

The two flat mirrors form the pair M2 and M3. They are positioned initially as shown in FIG. 5, one above the other, with a small space between them. The entry 1 and exit points 2 are positioned in such a way that part of the mirror M'1 is located between them. As such, the reflection points are kept in the cell.

These two mirrors are fixed by means of a flexible mechanical part which allows the adjustment of M3 relative to M2 along a single rotation axis while ensuring a very high level of rigidity outside this rotation.

This part is pierced by two holes which allow the beam to enter and exit the cell. An adjusting screw 3 and a spring stop make it possible to control M3. The two mirrors are glued directly to this part, M1 to the stationary part and M3 to the moving part. In order to ensure the correct orientation of the two mirrors, they are firstly placed with their reflective surface facing down on a flat reference surface (glass plate). The mechanical part, to which glue has previously been applied, is placed onto the back of the mirrors.

We have described here some embodiments in which the radii of curvature of the two mirrors M2 and M3 are identical and are located at an equal distance from the first mirror M1. The person skilled in the art will understand that the invention is not limited to this embodiment and also functions when the mirrors have different radii of curvature and are not at an equal distance from the first mirror M1. In general, for a mirror M2 having a radius of curvature R2 and located at a distance d2 from the mirror M1 and a third mirror M3 having a radius of curvature R3 and located at a distance d3 from the mirror M1, it is also possible to verify the stability conditions for the two cells formed according to the invention.

This is obtained when the first M1 and the second M2 mirrors are such that $$0 < \left(1 - \frac{d_2}{R_1}\right)\left(1 - \frac{d_2}{R_2}\right) < 1$$

and the first mirror M1 and the third mirror M3 are arranged in such a way that $$0 < \left(1 - \frac{d_3}{R_1}\right)\left(1 - \frac{d_3}{R_3}\right) < 1.$$

When the two cells formed are at an equal distance d from the mirror M1 and the radii of curvature R2 and R3 are equal to a radius R, these two conditions are equivalent. Remarkable configurations therefore exist which give the system great optomechanical stability when two mutually prime whole numbers K and N exist such that:

$$\cos\left(\frac{K\pi}{N}\right) = \sqrt{\left(1 - \frac{d}{R_1}\right)\left(1 - \frac{d}{R}\right)}.$$

The invention claimed is:

1. A multiple reflection optical system comprising a light beam input means (E) and an output means (S); and a first mirror (M1) having a radius of curvature R1, said first mirror being arranged opposite and at a distance d2 from a second mirror (M2) having a second radius of curvature R2 and opposite and at a distance d3 from a third mirror (M3) having a third radius of curvature R3, the first mirror (M1) and the second mirror (M2) being arranged in such a way that $$0 < \left(1 - \frac{d_2}{R_1}\right)\left(1 - \frac{d_2}{R_2}\right) < 1,$$

and the first mirror (M1) and the third mirror (M3) being arranged in such a way that $$0 < \left(1 - \frac{d_3}{R_1}\right)\left(1 - \frac{d_3}{R_3}\right) < 1,$$

the first mirror (M1) and the second mirror (M2) forming a first optical cell having a first optical axis, the first mirror (M1) and the third mirror (M3) forming a second optical cell having a second optical axis, said first and second optical axes being separate, the radii of curvature R1, R2, R3 and the distances d2 and d3 not being simultaneously equal, said first and second optical cells being arranged in such a way that the light beam is contained in the optical system between the input means and the output means.

2. The multiple reflection optical system according to claim 1, further comprising a means for varying the directions of said first and second optical axes.

3. The multiple reflection optical system according to claim 1, wherein said second (M2) and third (M3) mirrors are flat mirrors which are inclined relative to one another, and in that the first mirror (M1) is a spherical mirror.

4. The multiple reflection optical system according to claim 1, wherein said second (M2) and third (M3) mirrors are spherical mirrors which are inclined relative to one another.

5. The multiple reflection optical system according to claim 4, wherein the two radii of curvature R2 and R3 are substantially equal.

6. The multiple reflection optical system according to claim 5, wherein the second (M2) and third (M3) mirrors correspond to the lower part and to the upper part of one and the same spherical mirror that has been cut.

7. The multiple reflection optical system according to claim 1, wherein the distances d2 and d3 are substantially equal to a distance d, and in that the radii of curvature R2 and R3 are substantially equal to a radius R, the first, second and third mirrors furthermore being arranged in such a way that two mutually prime whole numbers K and N exist such that:

$$\cos\left(\frac{K\pi}{N}\right) = \sqrt{\left(1 - \frac{d}{R_1}\right)\left(1 - \frac{d}{R}\right)}.$$

8. The multiple reflection optical system according to claim 1, wherein the second mirror (M2) and the third mirror (M3) each have a straight edge and are joined by said edges and without touching one another, said edges being substantially parallel to the line passing through the intersection of the two optical axes with the second mirror (M2) and the third mirror (M3).

9. The multiple reflection optical system according to claim 8, wherein the light beam input means (E) is positioned in such a way as to generate a row of substantially focused reflection points along the edge of at least one of said second (M2) and third (M3) mirrors.

* * * * *